United States Patent [19]
Kozak et al.

[11] Patent Number: 6,121,299
[45] Date of Patent: Sep. 19, 2000

[54] MODULATING INFLAMMATION WITH CYTOCHROME P-450 ACTIVATORS AND INHIBITORS

[75] Inventors: Wieslaw Kozak; Matthew J. Kluger; Yohannes Tesfaigzi, all of Albuquerque, N. Mex.

[73] Assignee: Lovelace Respiratory Research Institute, Albuquerque, N. Mex.

[21] Appl. No.: 09/281,439

[22] Filed: Mar. 30, 1999

Related U.S. Application Data

[60] Provisional application No. 60/079,882, Mar. 30, 1998, and provisional application No. 60/110,046, Nov. 24, 1998.

[51] Int. Cl.[7] .................. A61K 31/41; A61K 31/415; A61K 31/24; A61K 31/235; A61K 31/195
[52] U.S. Cl. .................. 514/359; 514/396; 514/399; 514/534; 514/543; 514/563
[58] Field of Search .................. 514/563, 543, 514/534, 399, 396, 359

[56] References Cited

U.S. PATENT DOCUMENTS

| | | |
|---|---|---|
| 5,643,936 | 7/1997 | Halperin . |
| 5,658,881 | 8/1997 | Gelland et al. . |

FOREIGN PATENT DOCUMENTS

| | | |
|---|---|---|
| 60-228414A | 11/1985 | Japan . |
| 4154736A | 5/1991 | Japan . |

OTHER PUBLICATIONS

Aboiteux–Antoine, et al., "Comparative Induction of Drug–metabolizing Enzymes by Hypolipidaemic Compounds," *Gen. Pharmac.*, vol. 20, No. 4, pp. 407–412 (1989).

Holtzman, M.J., et al., "Arachidonic Acid Metabolism in Airway Epithelial Cells," *Annu. Rev. Physiol.*, vol. 54, pp 303–329 (1992).

Hudson, A.R., et al., "Granulocyte Recruitment to Airways Exposed to Endotoxin Aerosols," *Amer. Rev of Respir. Disease*, vol. 115, pp 89–75 (1977).

Ibrado, A.M., et al., "Bcl–$x_L$ Overexpression Inhibits Progression of Molecular Events Leading to Paclitaxel–Induced Apoptosis of Human Acute Myeloid Leukemia," *Cancer Res.*, vol. 57, pp 1109–1115 (Mar. 15, 1997).

Kroemer, G., et al., "The Proto–Oncogene Bcl–2 and Its Rolein Regulating Apoptosis," *Nature Medicine*, vol. 3, No. 6, pp 614–620 (Jun. 1997).

Levy, F.E., et al., "Modification of Inflammatory Processes by Phenobarbital in Rats," *Inflammation*, vol. 15, No. 6, pp 471–480 (1991).

McGiff, J.C., et al., "Cytochrome P–450 Metabolism of Arachidonic Acid," *Annu. Rev. Pharmacol. Toxicol.*, vol. 31, pp 339–369 (1991).

Marder, P., et al., "Blockade of Human Neutrophil Activation by Ly292111 . . . " *Biochem. Pharmacol.*, vol. 49, pp 1683–1690 (1995).

Mathews, J.M., et al., "Inactivationof Rabbit Pulmonary Cytochrome P–450 in Microsomes and Isolated Perfsed Lungs by the Suicide Substrate 1–Aminobenzotriazole," *J. Pharm. and ExperimentalThera.*, vol. 235, No. 1, pp 186–190 (1985).

Meier, R.W., et al., "Inhibition of the Arachidonic Acid Pathway Prevents Induction.." *J. Cell. Phys.*, vol. 165, pp 62–70 (1995).

Meschter, C.L., et al., "A 13–Week Toxicologic and Pathologic Evaluation . . . " *Fund. and Appl. Toxi.*, vol. 22, pp 369–381 (1994).

Morgan, E.T., et al., "Regulation of Cytochromes P450 during Inflammation and Infection," *Drug Metabolism Rev.*, vol. 29, No. 4, pp 1129–1188 (1997).

Nagata, S., "Fas–Mediated Apoptosis," *Adv. Exp. Med. Biol.*, vol. 46, pp 119–124 (1996).

Perdik, P., et al., "Arachidonic Acid is Metabolized by Cytochrome–P450 in the Rabbit Lung," *Am. Rev. Respir. Dis.*, vol. 147, p. A920 Abstract (1993).

Philpot, R.M., et al., "Role of Cytochrome P–450 and Related Enzymes in the Pulmonary Metabolism of Xenobiotics," *Envir. Health Pers.*, vol. 55, pp 359–367 (1984).

Reed, J.C., "Double Identity for Proteins of the Bcl–2 Family," *Nature*, vol. 387, pp 773–776 (1997).

Rylander, R., et al., "Pulmonary Function and symptoms After Inhalation of Endotoxin," *Am. Rev. Respir. Dis.*, vol. 140, pp 981–996 (1989).

Sandstrom, T., et al., "Lipopolysaccharide (LPS) Inhalation in Healthy subjects Increases Neutrophils, Lymphocytes and Fibronectin Levels in Bronchoalveolar Lavage Fluid," *Eur. Respir. J.*, vol. 5, pp 992–996 (1992).

Schilter, B., et al., "Regional Distribution and Expression Modulation of Cytochrome P–450 and Epoxide Hydrolase mRNAs in Rat Brain," *Mol. Pharmacol.*, vol. 44, pp 990–996 (1993).

Shannon, V.R., et al., "Histochemical Evidence for Induction of Arachidonate 15–Lipozygenase in Airway Disease," *Am. Rev. Repir. Dis.*, vol. 147, pp 1024–1028 (1993).

Streiter, R.M., et al., "Acute lung Injury: The Role of cytokines in the Elicitation of Neutrophils," *J. Inves. Med.*, vol. 42, No. 4, pp 640–651 (Dec. 1994).

Tesfaigzi, J., et al., "Induction of EGF Receptor and erbB–2 During Endotoxin–induced Alveolar Type II Cell Proliferation in the Rat Lung," *Int. J. exp. Path.*, vol. 77, pp 143–154 (1996).

Uhlig, S., et al., "Cyclooxygenase–2–Dependent Bronchoconstriction if Perfused Rat LungsExposed to Endotoxin," *Mol. Med.*, vol. 3, No. 3, pp 373–383 (May 1996).

(List continued on next page.)

*Primary Examiner*—William R. A. Jarvis
*Attorney, Agent, or Firm*—Rod D. Baker

[57] ABSTRACT

This invention relates to methods of modulating inflammation in mammals. Inflammation is modulated by regulating the cytochrome P-450 pathway. Inflammation is reduced by treating the subject with substances, such as bezafibrate and clofibrate, which induce the P-450 pathway. Inflammation is promoted by treating the subject with substances, such as proadifen, econazole, and clotrimazole, which inhibit the cytochrome P-450 pathway.

11 Claims, 14 Drawing Sheets

OTHER PUBLICATIONS

Zeldin, D.C., et al., "The Rabbit Pulmonary Cytochrome P450 Arachidonic Acid Metabolic Pathway: Characterization and Significance,". *clin. Invest.*, vol. 95, pp 2150–2160 (May 1995).

Amacher, D.E., "Hepatic Microsomal Enzyme Induction, Beta Oxidation, and Cell Proliferation Following Administration of Clofibrate, Gemfibrozil or Bezafibrate in the CD Rat," *Toxicology and applied Pharmacology*, vol. 142, pp 143–150 (1997).

Baggiolini, M., et al., "Neutrophil–Activating Peptide–I/Interleukin, 8, a Novel Cytokine That Activates Neutrophils," *J. Clin. Invest.*, vol. 84, pp 1045–1049 (1989).

Brigham, K.L., et al., "State of Art: Endotoxin and Lung Injury," *Am. Rev. Respir. Dis.*, vol. 133, pp 913–927 (1986).

Cai, Y., et al., "Effects of Acetylsalicylic Acid on Parameters Related to Peroxisome Proliferation in Mouse Liver," *Biochem. Pharm.* vol. 47, No. 12, pp 2213–2219 1994).

Capdevila, J.H., et al., "Cytochrome P450 and the Metabolism of Arachidonic Acid and Oxygenated Eicosanoids," *Cytochrome P450: Structure, Mechamism, and Biochemistry*, Ortiz de Montellano PR, Ed., $2^{nd}$ Ed. Plenum Press, New York pp 443–471 (1995).

Fogh, K., et al., "Interleukin–8 Stimulates the Formation of 15–Hydroxyl–Eicosatetraenoic Acid by Human Neutrophils in vitro", *Agents Actions*, vol. 35, pp. 239–247 (1992).

Guengerich, F.P., et al., "Preparation and Properties of Highly Purified cytochrome P–450 and NADPH–Cytochrome P–450 Reductase from Pulmonary Microsomes of Untreated Rabbits," *Mol. Pharm.*, vol. 13, pp. 911–923 (1977).

Harkema, J.R., et al., "In Vivo Effects of Endotoxin on Intraepithelial Mucosubstances in Rat Pulmonary Airways," *Am. J. of Path.*, vol. 141, No. 2, pp 307–317 (1992).

Henderson, W.R., Jr. "Eicosanoids and Platelet–Activating Factor in Allergic Respiratory Diseases," *Am. Rev. Respir. Dis.*, vol. 132, pp S86–S90 (1991).

Holtzman, M.J., "State of the Art: Arachidonic Acid Metabolism," *Am. Rev. Respir. Dis.*, vol. 143, pp. 188–203 (1991).

Kozak, W., et al., "Soluable Tumor Necrosis Factor Alpha Receptor Prevents Decrease of Body Temperature in Mice Treated with Indomethacin and Lipopolysaccraride," Ann. NY Acad. Sci., vol. 813, pp 264–271 (Mar. 15, 1997).

Kozak, W., et al., Dietary n–3 Fatty Acids Differentially Affect Sickness Behavior in Mice During Local and Systemic Inflammation, *Am J. Physiol*, vol. 272, pp R1298–R1307 (1977).

Kozak, W., et al., "Attenuation of Lipopolysaccharide Fever in Rats by Protein Kinase C Inhibitor", *Am. J. Physiol.*, vol. 273, No. 42, pp R873–R879 (1997).

Kozak, W., et al., "Sickness Behavior in Mice Deficient in Interleukin–6 During Turpentine Abscess and Influenza Pneumonitis,"*Am. J. Physiol.*, vol. 272, pp R621–R630 (1997).

Kozak, W., "Regulated Decreases in Body Temperature," *Fever: Basic Mechanisms and Management*, (P.A. Mackowiak, ed.) Lippincott–Raven Publ, Phila PA, pp 467–478 (1977).

Kluger, M.J. et al., "The Adaptive Value of Fever," *Basic Mechanisms and Management* (P.A. Mackowiak, Ed.) Lippincott–Raven Publ., Phila PA, pp 255–266 (1997).

Kluger, M.J., et al., "Effect of Heat Stress on LPS–Induced Fever and Tumor Necrosis Factor," *Am. J. Physiol.* vol. 273, No. 42, pp R858–R863 (1997).

Leon, L.R., et al., "Altered Acute Phase Responses to Inflammation in IL–1 and TNF Receptor Knockout Mice," *Ann. NY Acad. Sci.*, vol. 813, pp. 244–254 (1997).

Leon, L.R., et al., "Exacerbated Febrile Responses to LPS, But Not Turpentine, in TNF Double Receptor–Knockout Mice," *Am. J. Physiol.*, vol. 272, pp R563–R569 (1997).

Moochhala, S.M. et al., "Induction and Depression of Cytochrome P–450–Dependent Mixed–Function Oxidase by a Cloned Consensus Alpha–Interferon (IFN–alpha CON1) in the Hamster," *Biochem. Pharmacol.*, vol. 38, No. 3, pp 439–447 (Feb. 1, 1989) Abstract Only.

Nakashima, T., et al., "Antipyretic Effect of Metabolite(s) of Cytochrome P450 of Arachidonic Acid Cascade in Rats," $67^{th}$ *Annual Meeting of Zoological Soc. of Japan*, Sapporo, Japan (Zoological Science, Tokyo) Sep. 18–20, 1996 Abstract Only.

Nakashima, T., et al., Inhibitors of Cytochrome P–450 Augment Fevere Induced by Interleukin–1 Beta, Am. J. Physiol., (5 pt 2), vol. 271, pp R1274–R1279 (Nov 1997) abstract and paper.

Raffali, F., et al., "Measurement and Modulation of Cytochrome–P450–Dependent Enzyme Activity in Cultured Human Keratinocytes," *Skin Pharmacol.*, vol. 7, No. 6, pp 345–354 (1994) Abstract Only.

Simpson A.E., et al., "Placental Transfer of the Hypolipidemic Drug, Clofibrate, Induces CYP4A Expression in 18.5–day Fetal Rats," *Drug. Metab. Dispos.*, vol. 24, No. 5, pp 547–554 (May 1996) Abstract Only.

Soszynski, D., et al., "Open Field–Induced Rise in Body Temperature and plasma IL–6 Is Mediated by Beta–Adrenoceptors in the Brain," *Ann NY Acad. Sci.*, vol. 813, pp. 413–419 (1997).

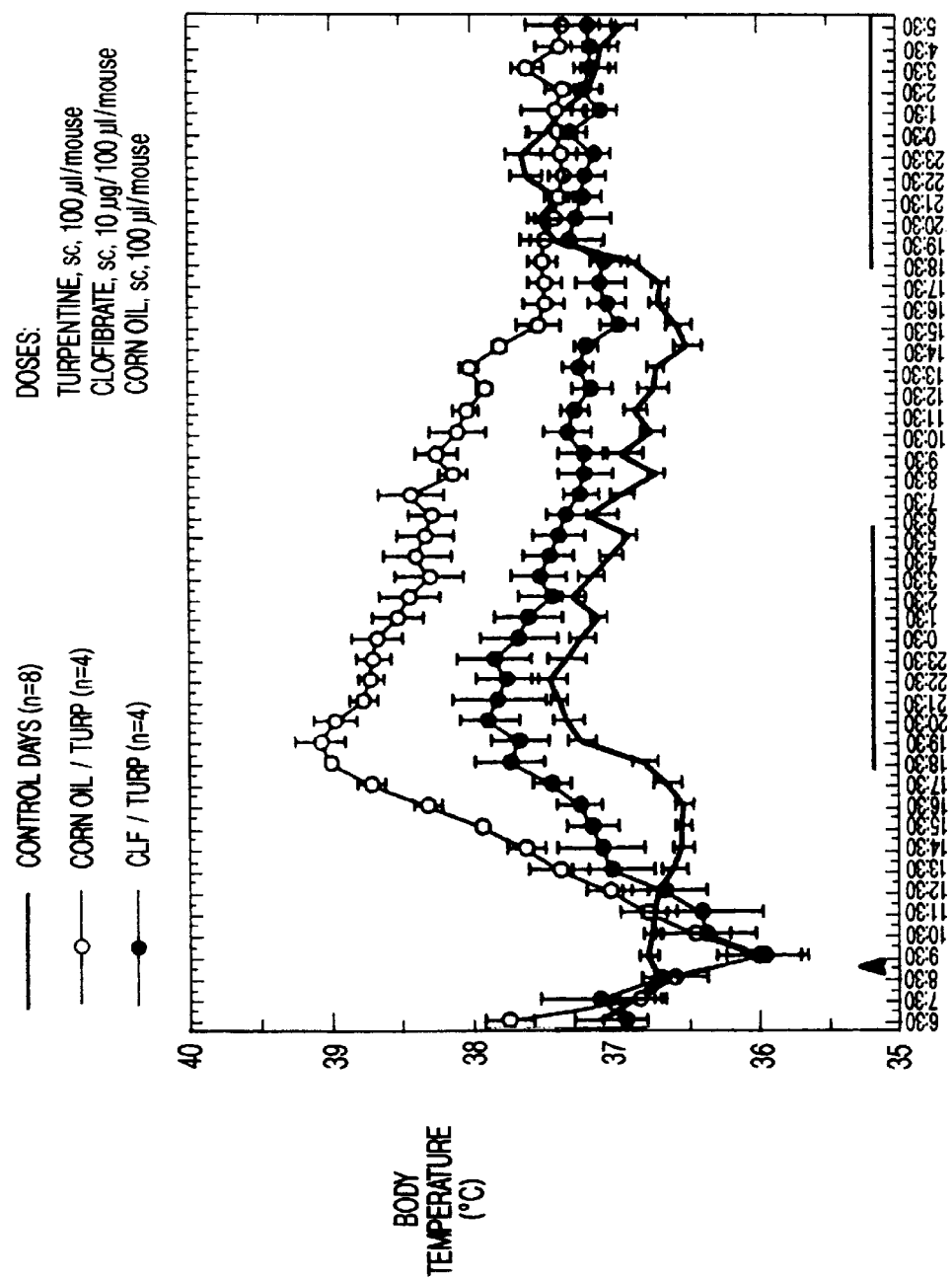

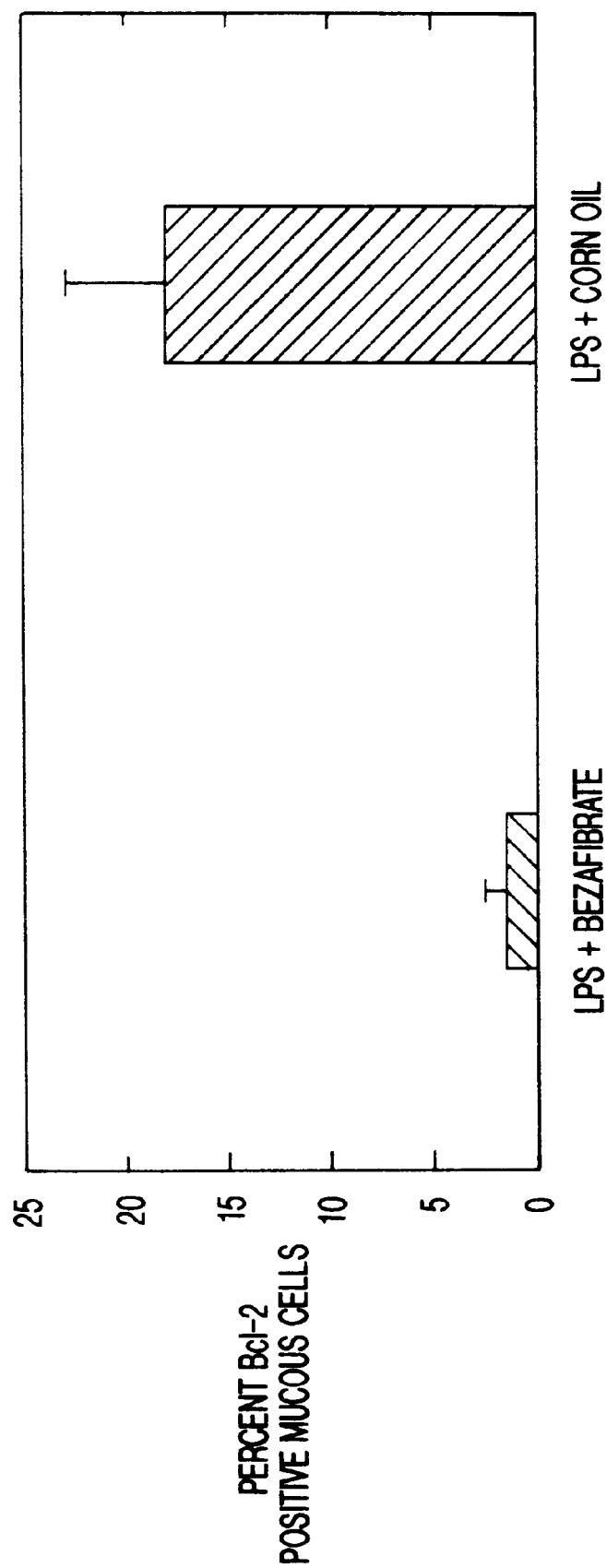

MODULATING INFLAMMATION WITH CYTOCHROME P-450 ACTIVATORS AND INHIBITORS

CROSS-REFERENCE TO RELATED APPLICATIONS

This application claims the benefit of the filing of U.S. Provisional Patent Application Ser. No. 60/079,882, entitled "A Novel Method to Modulate Inflammation," filed on Mar. 30, 1998, and of the filing of U.S. Provisional Patent Application Ser. No. 60/110,046, also entitled "A Novel Method to Modulate Inflammation," filed on Nov. 24, 1998. The specifications of both such applications are incorporated herein by reference.

GOVERNMENT RIGHTS

The United States Government has certain rights to this invention pursuant to Contract No. NIH-AI-256556-07 awarded by the National Institute of Health.

BACKGROUND OF THE INVENTION

1. Field of the Invention (Technical Field)

The present invention relates to the control and treatment of inflammation in mammals, particularly to a method of modulating inflammation with cytochrome P-450 inducers and inhibitors.

2. Background Art

Major advances over the past several years have dramatically enhanced the recognition that inflammation is integral to a broad spectrum of diseases. Inflammation plays a central role in various pulmonary disorders. One of the best examples in this category is asthma. The airway obstruction that defines asthma is associated with inflammation in the lung. Asthma and chronic bronchitis alone may affect 25 million persons in the United States.

Much progress has been made toward understanding the mechanisms of airway inflammation. Information has evolved regarding, among others, airway production of chemokines, cytokines and growth factors, expression of adhesion molecules, and generation of lipid mediators that all orchestrate and control the initiation and propagation of lung inflammation. Based on understanding these pro- and anti-inflammatory mechanisms, new therapeutic approaches are being developed to prevent lung inflammation.

As constituents of endotoxin of the cell walls of gram-negative bacteria, lipopolysaccharides are potent environmental agents that have pro-inflammatory properties and can obstruct and inflame airways. It is known that LPS have a broad range of actions, including the activation of endothelial and epithelial cells, neutrophils, and alveolar macrophages, and the induction of cytokines, prostaglandins, leukotrienes and other inflammatory mediators. Airway infections induced by endotoxin-laden bacteria in hospitalized patients are associated with fever, influx of inflammatory cells (particularly neutrophils), and increased production of respiratory mucus. Previous studies have demonstrated that intra-airway exposure to LPS induces inflammatory changes in the rat and mouse similar to changes in patients with chronic bronchitis, bronchopneumonia, and cystic fibrosis. Hudson A. R., et al., "Granulocyte recruitment to airways exposed to endotoxin aerosols", Am. Rev. Respir. Dis. 115:89–95 (1977); Brigham K. L., et al., "Endotoxin and lung injury", Am. Rev. Respir. Dis. 133:913–927 (1986); Rylander R., et al., "Pulmonary function and symptoms after inhalation of endotoxin", Am. Rev. Respir. Dis. 140:981–996 (1989); Sandstrom T., et al., "Lipopolysaccharide (LPS) inhalation in healthy subjects increases neutrophils, lymphocytes and fibronectin levels in bronchoalveolar lavage fluid", Eur. Respir. J. 5:992–996 (1992); Harkema J. R., et al., "In vivo effects of endotoxin on intraepithelial mucosubstances in rat pulmonary airways. Quantitative histochemistry", Am. J. Pathol. 141:307–317 (1992); Strieter R. M., et al., "Acute lung injury: The role of cytokines in the elicitation of neutrophils", J. Invest. Med. 42:640–651 (1994); Tesfaigzi J., et al., "Induction of EGF receptor and erbB-2 during endotoxin-induced alveolar type II cell proliferation in the rat lung", Int. J. Exp. Path. 77:143–154 (1996).

Arachidonic acid can be oxidized by three enzymatic pathways. McGiff J. C., "Cytochrome P-450 metabolism of arachidonic acid", Annual Rev. Pharmacol. Toxicol. 31:339–369 (1991); Capdevila J. H., et al., "Cytochrome P450 and the metabolism of arachidonic acid and oxygenated eicosanoids", Cytochrome P450: Structure, Mechanism, and Biochemistry. Ortiz de Montellano PR, ed., $2^{nd}$ Ed. Plenum Press, New York, pp. 443–471 (1995). Cyclooxygenases (COX) metabolize arachidonic acid to prostaglandins, thromboxane, and prostacyclin. Lipoxygenases (LOX) convert arachidonic acid to leukotrienes and hydroperoxyeicosatetraenoic acids. P-450 monooxygenases catalyze the formation of epoxyeicosatrienoic acids, hydroxyeicosatetraenoic acids, and C19/C20 alcohols of arachidonic acid. Enhanced/altered metabolism of arachidonic acid via COX and LOX is intrinsic to every inflammatory process, including lung inflammation. Henderson W. R., "Eicosanoids and platelet-activating factor in allergic respiratory diseases", Am. Rev. Respir. Dis. 143:S86–S90 (1991); Holtzman M. J., "Arachidonic acid metabolism. Implications of biological chemistry for lung function and disease." Am. Rev. Respir. Dis. 143:188–203 (1991); Shannon V. R., et al., "Histochemical evidence for induction of arachidonate 15-lipoxygenase in airway disease", Am. Rev. Respir. Dis. 147:1024–1028 (1993); Uhlig S., et al., "Cyclooxygenase-2-dependent bronchoconstriction in perfused rat lung exposed to endotoxin", Mol. Med. 2:373–383 (1996).

Pharmacological inhibition of the expression of COX and LOX, as well as modulation of receptors of the respective eicosanoids, play a significant role in modern medicine. Although arachidonic acid can also be converted via P-450 monooxygenase, the significance of this pathway for inflammation has not been thoroughly investigated. However, inflammatory stimuli do affect the expression of various isoforms of cytochrome P-450, mostly in the liver. Morgan E. T., "Regulation of cytochromes P450 during inflammation and infection", Drug Metab. Rev. 29:1129–1188 (1997). Administration of phenobarbital reduces the severity of type II collagen-induced arthritis in the rat. Levy L. E., et al., "Modification of inflammatory process by phenobarbital in rats", Inflammation 15:471–480 (1991). Acetylsalicylic acid, a well known pharmacologic anti-inflammatory inhibitor of cyclooxygenases, has induced P-450 in mouse. Cai Y., et al., "Effect of acetylsalicylic acid on parameters related to peroxisome proliferation in mouse liver", Biochem. Pharmacol. 47:2213–2219 (1994).

As in the other tissues, a high level of COX and LOX has been repeatedly reported in the lung. Holtzman, M. J., "Arachidonic acid metabolism in airway epithelial cells", Annual Rev. Physiol. 54:303–329 (1992). The existence of a third pathway of arachidonic acid oxygenation in the lung—the cytochrome P-450 arachidonate monooxygenase/epoxygenase—was only recently documented. Perdik, P. et al., "Arachidonic acid is metabolized by cytochrome P-450 in the rabbit lung", *Am. Rev. Respir. Dis.* 147:A920 (1993); Zeldin, D. C., et al., "The rabbit pulmonary cytochrome P-450 arachidonic acid metabolic pathway: characterization and significance", *J. Clin. Invest.* 95:2150–2160 (1995). However, studies on pulmonary P-450s have a long history, and this enzymatic system plays a significant role in the biotransformation of xenobiotics including inhaled chemical carcinogens and lung toxins. Guengerich, F. P., "Preparation and properties of highly purified cytochrome P450 and NADPH-cytochrome P450 reductase from pulmonary microsomes of untreated rabbits", *Mol. Pharmacol.* 13:911–923 (1977); Philpot, R. M., et al., "Role of cytochrome P450 and related enzymes in the pulmonary metabolism of xenobiotics", *Environ. Health Perspect.* 55:359–367 (1984). In contrast to the role for COX and LOX, particularly COX-2 and 15-LOX, no information is available about the role of epoxygenase in lung inflammation.

It is known that interleukin-8 has a role in LPS-induced lung inflammation IL-8 was initially identified as a C—X—C chemokine on the basis of its ability to induce neutrophil activation and chemotaxis. Baggiolini, M., et al, "Neutrophil-activating peptide-1/interleukin 8, a novel cytokine that activates neutrophils", *J. Clin. Invest.* 84:1045–1049 (1989). The recruitment of neutrophils by IL-8, in addition to the action of other chemoattractants on neutrophils, is critical for the propagation of inflammation in the lung. Upon arrival at the lung, activated neutrophils induce pulmonary injury through the release of reactive metabolites and proteolytic enzymes.

Generation of IL-8 is associated with changes in activation of the enzymes involved in arachidonate cascade. Release of IL-8 by human airway smooth muscle cells is stimulated by prostaglandin $E_2$ (PGE$_2$) and leukotriene $B_4$ (LTB$_4$), and bradykinin-induced production of IL-8 in those cells can be inhibited by COX-2 inhibitors. Interestingly, however, 5,8,11,14-eicosatetraynoic acid (ETYA), an inhibitor of the all three enzymes of the arachidonic acid pathway, and ketoconazole, an inhibitor of LOX and P-450 monooxygenase, increase the induced IL-8 RNA and the release of IL-8 in HL 60 cells. Meier R. W., et al., "Inhibition of the arachidonic acid pathway prevents induction of IL-8 mRNA by phorbol ester and changes the release of IL-8 from HL 60 cells: Differential inhibition of induced expression of IL-8, TNF-alpha, IL-1 alpha, and IL-1 beta", *J. Cell Physiol.* 165:62–70 (1995).

Enzymes of arachidonate metabolism are also involved in the action of IL-8 on neutrophils. IL-8 induces expression of COX-2 and LOX in human neutrophils, and IL-8-induced activation of neutrophils can be inhibited by the LTB$_4$ receptor antagonist. Fogh K., et al., "Interleukin-8 stimulates the formation of 15-hydroxy-eicosatetraenoic acid by human neutrophils in vitro", *Agents Actions* 35:227–231 (1992); Marder P., et al., "Blockade of human neutrophil activation by 2-[2-propyl-3-[2-ethyl-4-(4-fluorophyl)-5-hydroxyphenoxy]propoxy]benzoic acid (LY293111), a novel leukotriene B4 receptor antagonist", *Biochem. Pharmacol.* 49:1683–1690 (1995).

IL-8 not only promotes inflammation by recruiting neutrophils into the lungs, but also acts to suppress the leukocyte apoptosis. Neutrophil apoptosis is crucial in the resolution of inflammation. One factor that regulates apoptosis is the Bcl-2 gene family, and Bcl-2 extends cell survival under a wide range of stimuli, including infectious and inflammatory conditions. Reed, J. C., "Double identity for proteins of the Bcl-2 family", *Nature* 387:773–776 (1997); Ibrado A. M., et al., "Bcl-XL overexpression inhibits progression of molecular events leading to paclitaxel-induced apoptosis of human acute myeloid leukemia HL-60 cells", *Cancer Res.* 57:1109–1115 (1997); Kroemer G., "The proto-oncogene Bcl-2 and its role in regulating apoptosis", *Nat. Med.* 3:614–620 (1997). Bcl-2 expression is controlled by cytokines. Nagata S., "Fas-mediated apoptosis", *Adv. Exp. Med. Biol.* 406:119–124 (1996). For example, IL-10 suppresses neutrophil Bcl-2 expression and enhances neutrophil apoptosis, while IL-8 enhances Bcl-2 expression and suppresses neutrophil apoptosis.

Currently, anti-inflammatory drugs belong to two major classes—nonsteroidal anti-inflammatory drugs (NSAIDs), such as aspirin and ibuprofen, and glucocorticoids. In addition, there are a variety of anti-cytokine drugs in development as well as other drugs that block specific components of inflammation (e.g., anti-adhesion molecules). The NSAIDs are effective against some types of inflammatory processes, and work by inhibiting cyclooxygenase. However, this causes increased production of both lipoxygenase and cytochrome P-450. In some diseases (e.g., asthma), it is thought that the induction of lipoxygenase actually enhances the inflammatory response associated with the disease. Conventional NSAIDs are also problematic in that they are associated with other serious side-effects such as gastrointestinal bleeding and renal dysfunction. Glucocorticoids have many harmful and potentially life-threatening side-effects, including hypertension, hyperglycemia, peptic ulcers, myopathy, cataracts, osteoporosis and osteonecrosis, and growth retardation.

Against the foregoing, the present inventive therapeutic approach was developed. The present invention employs the anti-inflammatory mechanism of cytochrome P-450 inducers of lung inflammation, thereby avoiding some of the drawbacks of current modes of inflammation treatment.

SUMMARY OF THE INVENTION

Disclosure of the Invention

The invention is a method of modulating mammalian inflammation by modulating the cytochrome P-450 pathway. Preferably, modulating a mammal's cytochrome P-450 pathway comprises reducing inflammation by inducing the cytochrome P-450 pathway. More specifically, the step of inducing the cytochrome P-450 pathway comprises treating the mammal with a substance selected from the group consisting of bezafibrate and clofibrate. The step of reducing inflammation may include the step of injecting the substance to reduce inflammation in the mammal's lungs. Alternatively, modulating the mammal's cytochrome P-450 pathway may comprise increasing inflammation by inhibiting the cytochrome P-450 pathway. The step of inhibiting the cytochrome P-450 pathway comprises treating the mammal with a substance selected from the group consisting of proadifen, econazole, clotrimazole, and 1-aminobenzotriazole.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 5A is a graph showing plots of body temperature versus time in mice, also illustrating the effects of clofibrate;

FIG. 12 is a micrograph and bar graph depicting the effect of bezafibrate treatment on the expression of Bcl-2 in lipopolysaccharide-induced metaplastic mucous cells of axial airways of a rat.

DESCRIPTION OF THE PREFERRED EMBODIMENTS

Figure 1:
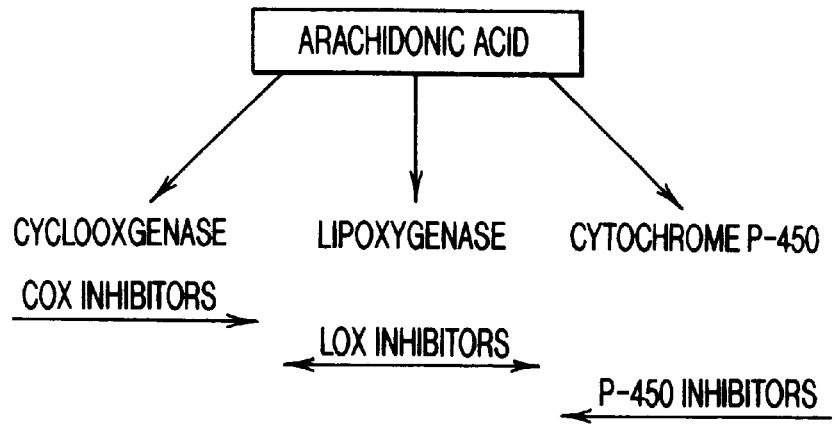
FIG. 1 is a prior art diagram illustrating that the pool of free arachidonic acid can be shifted by cyclooxygenase inhibitors or monooxygenase inhibitors.

Best Modes for Carrying Out the Invention

Broadly described, the present invention includes a method of modulating, and therefore treating, inflammation in living mammals. The modulation of inflammation according to the present invention has particularly beneficial applications in the treatment of lung inflammations, most especially asthma, as well as the treatment of other inflammations generally.

Decreases in locomotion and increases in prostaglandins and fever are often symptoms of inflammation. Mild inflammation causes decreased locomotor activity and release of moderate amounts of prostaglandins. More severe inflammation causes the above changes along with fever, sleepiness, and associated "sickness behaviors" (e.g., decreased exploratory behavior). We have determined that inhibition of cytochrome P-450 exacerbates symptoms of inflammation. More importantly, symptoms of inflammation can be suppressed by stimulating cytochrome P-450.

Inflammation can be intentionally induced in mammals. Injection of lipopolysaccharides, turpentine, or other inflammatory stimuli, causes a variety of inflammatory responses and alterations (e.g., hypotension, increase of vascular permeability, leukocyte accumulation, fluid and electrolyte alterations, activation and release of humoral factors such as complement, histamine, serotonin, cytokines and transforming growth factors, phospholipase $A_1$, prostaglandins, leukotrienes, platelet activating factor, degranulation of neutrophils and release of lysosomal hydrolases). Some of these are beneficial to the host and some are harmful.

Although Nakashima, et al., "Inhibitors of cytochrome P-450 augment fever induced by interleukin-1B," *Am. J. Physiol.* 40:R1274–R1279 (1996) showed that injection of inhibitors of cytochrome P-450 augmented fever due to injection of IL-1, their work was restricted to proposed antipyretic actions of cytochrome P-450. No suggestion was made that drugs that would induce cytochrome P-450 would therefore attenuate fever. There is little (if any) value in inducing larger fevers. In contrast, the present invention involves administration of drugs known to induce cytochrome P-450 to attenuate inflammation.

Accordingly, the present invention is founded upon the determination that cytochrome P-450 plays a key anti-inflammatory role. The invention thus will find utility in the development of novel pharmaceuticals, or new uses for existing drugs, that can modulate inflammation. In some cases it may be beneficial to the patient to block the cytochrome P-450 pathway, which would facilitate inflammation (e.g., in malnourished patients, some elderly). In other cases, it will be beneficial to facilitate or induce this pathway to suppress inflammation during such diseases as: Abscess, acute mountain sickness, Addison's disease, Alzheimer's disease, arthritis, asthma, autoimmune disorders, burn injury, cold symptoms (e.g., nasal congestion, aches), inflammatory bowel diseases (e.g., Crohn's disease), Ischemia-reperfusion injury, liver injury, neuropathies, ophthalmic inflammation, Parkinson's disease, septicemia, skin disorders (e.g., acne, scleroderma), and symptoms of sickness behavior (e.g., appetite, sleep, motor and cognitive activity).

It is noted, however, that there are important physiological distinctions between fever and inflammation that prevent diagnosis and/or treatment hypotheses from being immediately applicable from either one to the other. The molecular mechanisms of fever involve two types of endogenous mediators: selected cytokines, which are also known as endogenous pyrogens, and prostaglandins—metabolites of arachidonic acid. Currently, there are over sixty cytokines known to be released during inflammation. Those that are known to function as mediators of fever are only few—predominantly interleukin-1β, interleukin-6, tumor necrosis factor α, and macrophage inflammatory protein. Among numerous metabolites of arachidonic acid generated during various inflammations, only prostaglandin $E_2$ produced by cyclooxygenases is known to play a role in the generation of fever. Metabolites of lipoxygenases, the other system that metabolizes arachidonic acid, although vital for the induction of inflammation due to their potent chemotactic activity, do not seem to be important for the generation of fever. Thus fever utilizes only small number of mediators involved in inflammation.

Inflammation appears to be more complex than fever, and involves a broad spectrum of mediators including other cytokines, immune complexes, prostaglandins and other eicosanoids, histamine, serotonin, complement, bradykinin, chemotaxic-, lysosomal- and endothelial adhesion-related systems, among others.

During inflammation, heat is regarded as a local elevation of temperature of inflamed tissue/organ due to dilation of arterioles and increase of local blood flow. Increased local metabolism, due to the influx of white blood cells into the inflamed area may also contribute to the rise in local temperature. Fever, on the other hand, is a systemic response to microbial, parasite, and toxin invasions, and is mediated by the endogenously (i.e., by the host) produced factors. These factors may also be generated during inflammation. The rise in body temperature during fever is caused by the upward re-setting of the thermostat for temperature regulation within the hypothalamus of the brain. This rise in "set-point" causes the host to shiver, decrease skin blood flow, and to use behavioral responses to raise core body temperature. Any attempt to physically cool the febrile (feverish) patient causes severe discomfort due to the regulated nature of fever (that is, once body temperature falls below the set-point temperature the person feels very cold). Conversely, one can cool an inflamed joint, without any generalized sense of discomfort. Thus, the causes of higher temperature are very different during inflammation and fever.

Moreover, inflammation is traditionally considered a localized protective response, which serves to destroy the injurious agent and/or the injured tissue. Although principally protective, exacerbated or chronic inflammation can be harmful to the host. Acute inflammation is characterized by the classical signs of pain (dolor), heat (calor), redness (rubor), swelling (tumor), and loss of function (functio laesa).

Fever sometimes accompanies inflammation. Inflammation may not always accompany fever. Under experimental conditions, one can induce fever in animals or people by intravenous injection of bacterial toxins. This may cause little or no localized inflammation, but may cause extremely high fevers. The presence of fever during a localized inflammation depends on the magnitude, acuteness, and a type (etiology) of trauma inducing the inflammation. For example, most allergic inflammations that may result in asthma are not commonly associated with fever. The piercing of the skin by a rose thorn will cause localized inflammation, but no fever. Localized inflammation caused by a single bee-sting does not normally result in fever. However, inflammation induced by a larger tissue necrosis produced by dozens of bee-stings, may be accompanied by fever.

There is only a partial overlap between the type of molecular signals that induce inflammation and those that cause fever. As a result, drugs that may block fever may only partially attenuate inflammation. For example, acetaminophen, as well as many other antipyretic drugs, may block fever in its entirety, yet has very limited anti-inflammatory action. Antihistamines may attenuate inflammation caused by allergy, yet they have absolutely no effect on fever. Consequently, although fever and inflammation share some similar characteristics, they differ in many ways. Fever may occur without inflammation; inflammation may occur without fever. Central re-setting of the thermostat causes the rise in body temperature during fever; the rise in temperature in an inflamed area is due to local changes. And, perhaps most importantly, drugs that may attenuate inflammation may not have any measurable impact on fever and vice versa. There is no ustification, therefore to automatically conclude that a drug that modulates fever would necessarily modulate inflammation.

As mentioned, inflammation is caused by release into tissues of pro-inflammatory cytokines (e.g., tumor necrosis factor IL-1B and others) as well as by the release of prostaglandins. Prostaglandins arise as a result of the release of arachidonic acid and the actions of cyclooxygenases. However, as shown in FIG. 1 (from the prior art) depending on the pharmacologic treatment (i.e., inhibitor used), the pool of free arachidonic acid (generated after activation of phospholipase $A_2$ by immunostimulators) can be shifted (arrows) either to the right (by cyclooxygenase inhibitors) or to the left (by using cytochrome P-450 monooxygenase inhibitors). McGiff J. C., "Cytochrome P-450 metabolism of arachidonic acid", *Annual Rev. Pharmacol. Toxicol.* 31:339–369 (1991).

We have determined that inhibitors and inducers of the cytochrome P-450 pathway modulate inflammatory processes. Using mice and rats implanted with biotelemeters that permit the monitoring of body temperature and locomotor activity in unrestrained animals (as indicators of inflammation), and measurement of mortality and $PGE_2$ (a pro-inflammatory lipid), three determinations significant to the present invention have been made.

Figure 2:
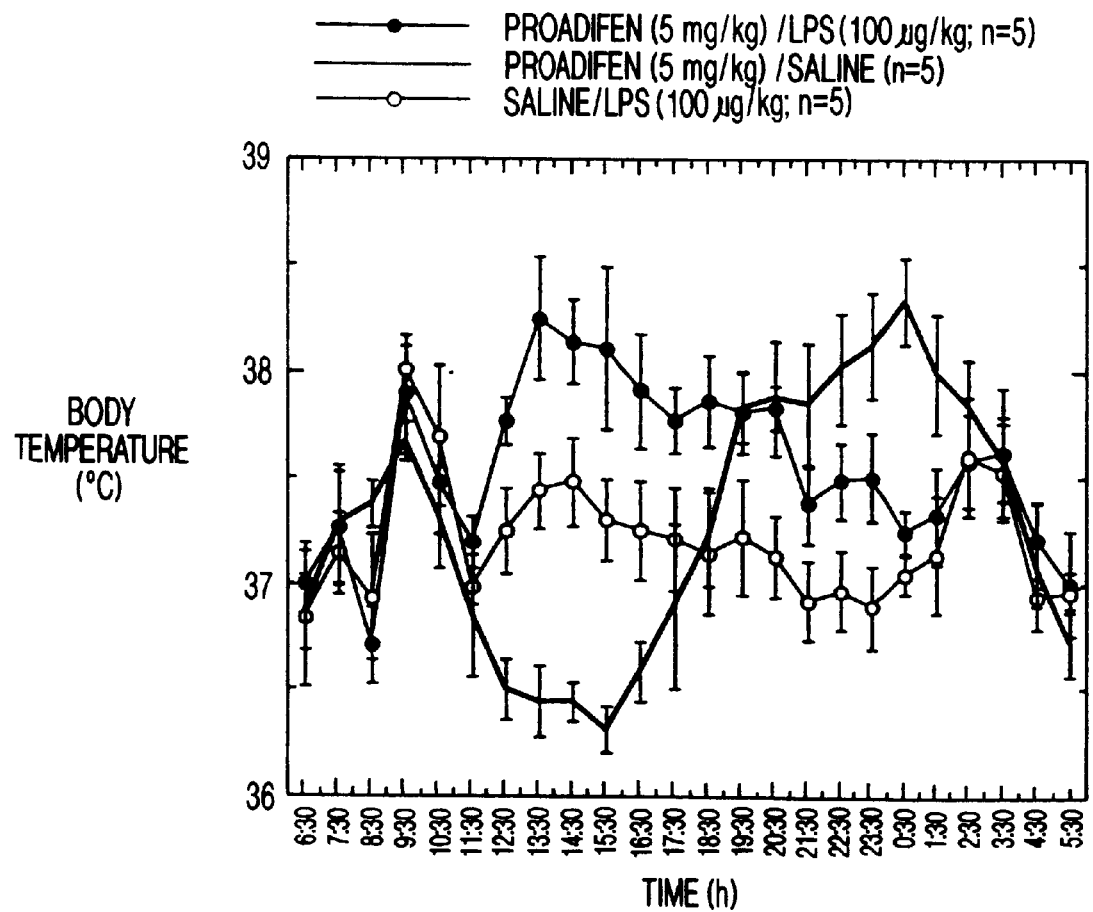
FIG. 2 is a graph showing plots of body temperature versus time in mice treated with proafiden, a cytochrome P-450 pathway inhibitor.

First, inhibitors of cytochrome P-450 potentiate fever in mice and rats caused by intraperitoneal (ip) injection of lipopolysaccharide. Reference is made to FIGS. 2 and 3. Three inhibitors were used to establish the findings displayed in FIGS. 2 and 3: proadifen, econazole and clotrimazole.

FIG. 2 shows the effect of proadifen (SKF 525-A; 5 mg/kg), an inhibitor of cytochrome P-450, on LPS (100 µg/kg)-induced changes in body temperature ($T_b$) in mice recorded over 24 hours. At 0900 hours (arrow) mice were ip injected with proadifen and/or saline as a control injection; thirty minutes later the mice were ip injected with LPS, an/or saline as a control injection. The numbers in parenthesis in FIG. 2 indicate sample size. All injections were made separately. Despite the LPS injection, mice injected with proadifen (5 mg/kg) and saline (solid line with no symbols in FIG. 2) displayed normal circadian rise in $T_b$ during the night. The black horizontal bar in FIG. 2 indicates the dark period in the 12/12 h light/dark cycle.

Figure 3A:
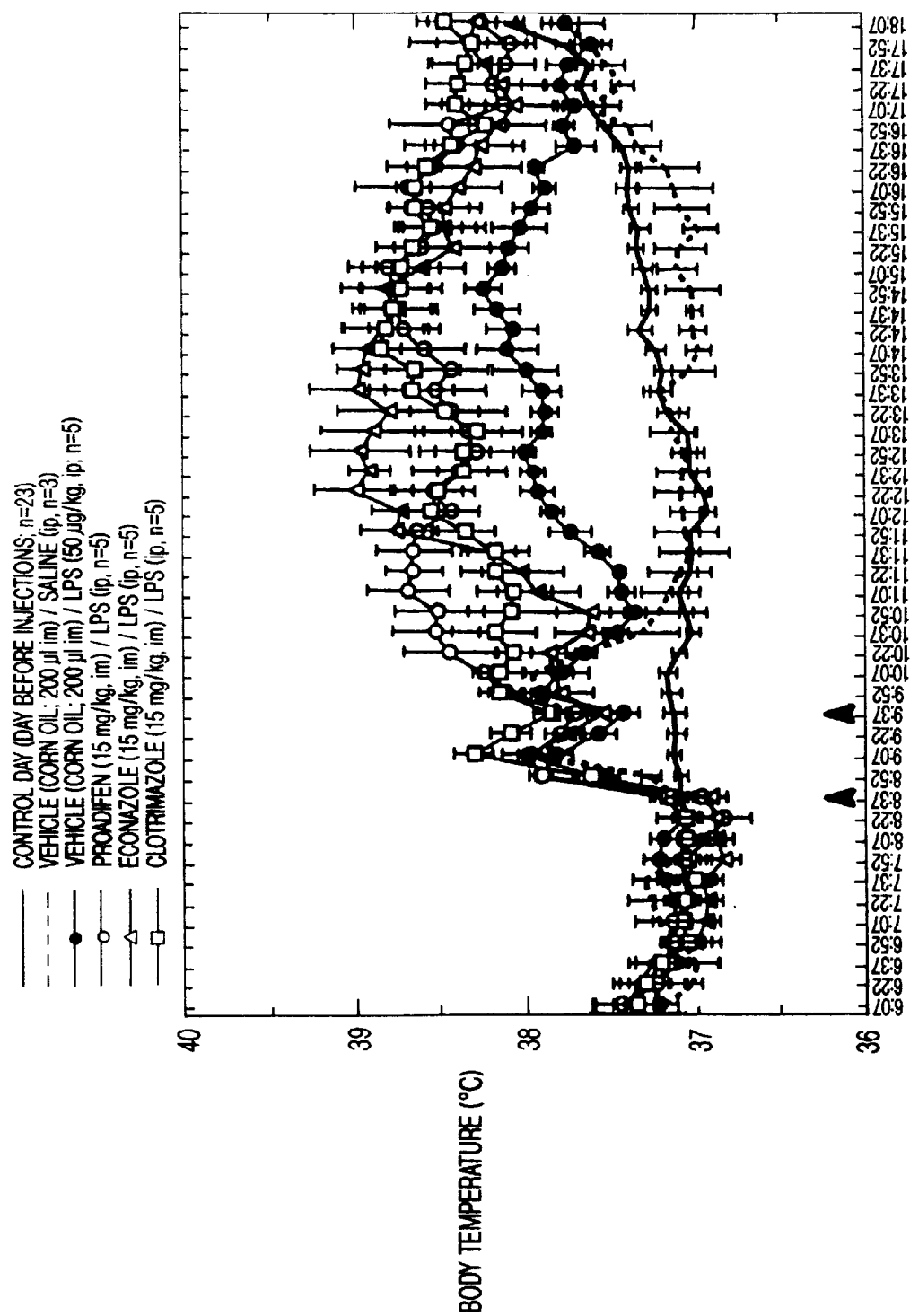
FIG. 3A is a graph showing plots of body temperature versus time in rats treated with cytochrome P-450 pathway inhibitors proadifen, econazole, and clotrimazole.
Figure 3B:
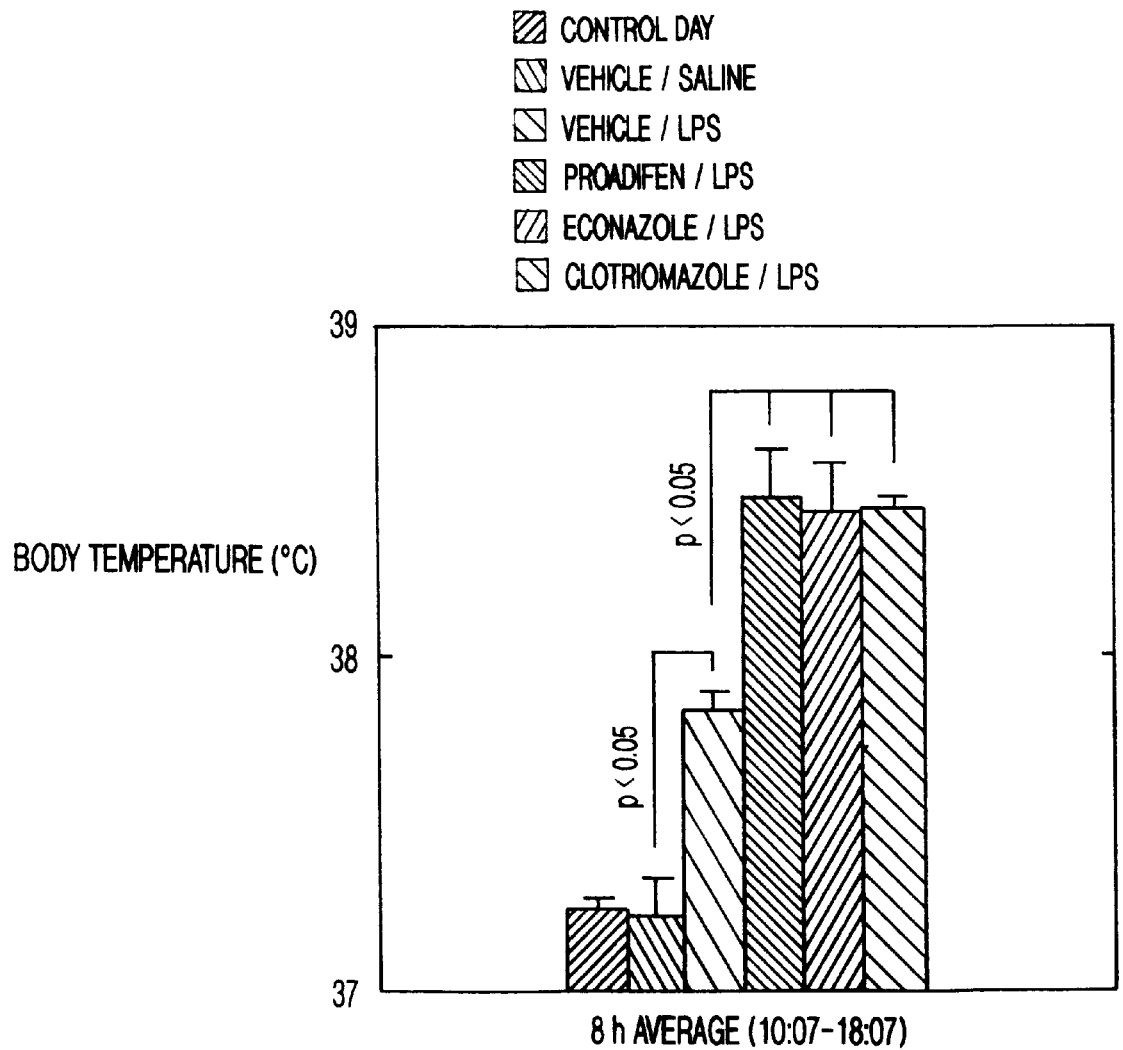
FIG. 3B is a bar graph of average body temperature versus time of rats treated with proadifen, econazole, and clotrimazole.

Reference also is made to FIGS. 3A and 3B. FIG. 3A shows changes of $T_b$ over time, and FIG. 3B shows the 8-hour average $T_b$, of rats intramuscular (im) injected at 0830 (left arrow) with the respective cytochrome P-450 inhibitor (proadifen, econazole, or clotrimazole, each at a dose of 15 mg/kg) and or control vehicle as shown, then one hour later at 0930 (right arrow) with an ip injection of LPS (50 µg/kg) and or saline as control. The stress-induced rise in $T_b$ during handling and initial injection with inhibitor is noted. The control injections did not affect a time course of normal $T_b$, as noted by comparing the dashed line versus the solid line with no symbols in FIG. 3A. Similarly, it was observed that cytochrome P-450 inhibitors (proadifen, econazole, or clotrimazole) injected alone did not influence normal $T_b$, although this data is not presented in FIGS. 3A or 3B for clarity of illustration. The ambient temperature was 25° C. (thermoneutral for rats). Values given are means of 15-minute averages ±SE. In the figures, the numbers in parenthesis indicate sample size.

FIG. 3B shows the average $T_b$ computed from 1000 h to 1800 h for the rats shown in FIG. 3A. A significant difference is noted ($p<0.05$; ANOVA followed by Fisher's PLSD) between the average $T_b$ of control injected animals, those injected with LPS and control vehicle, and those injected with LPS and cytochrome P-450 inhibitor(s).

Figure 4:
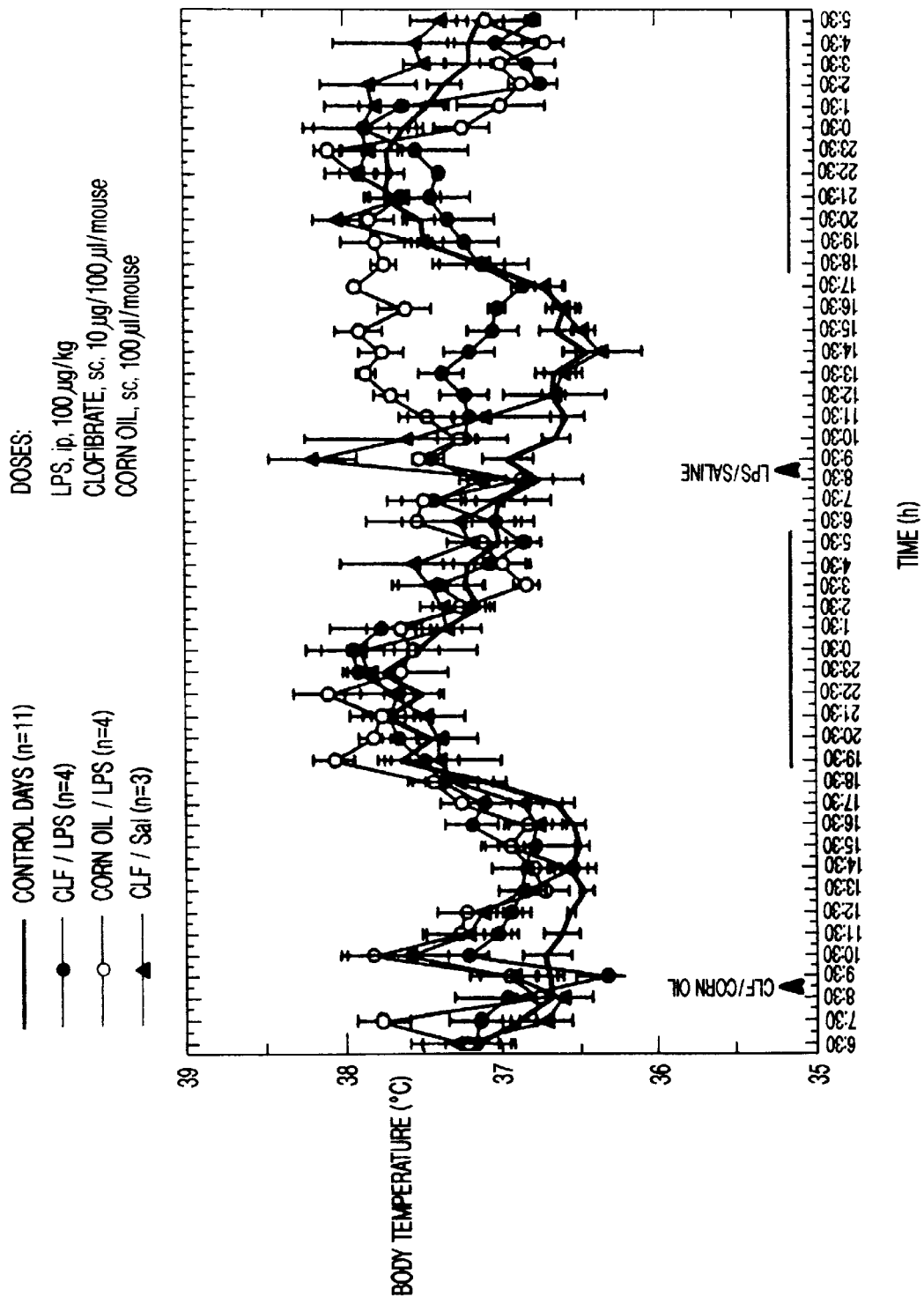
FIG. 4 is a graph showing plots of body temperature versus time in mice, illustrating the effects of clofibrate, a cytochrome P-450 inducer.

Furthermore, it was determined that a drug, clofibrate, which stimulates (and induces) the in vivo activity of cytochrome P-450 led to smaller fevers in mice caused by ip injection of LPS and subcutaneous (sc) injection of turpentine. Data in this respect is provided in FIGS. 4 and 5A. FIG. 4 illustrates the effect of clofibrate, a cytochrome P-450 inducer, on LPS (100 µg/kg)-induced changes of $T_b$ in mice. Clofibrate was injected 24 hours prior to LPS. At 0900 h (left arrow) mice were anesthetized (halothane) and sc injected with clofibrate (10 µl in 100 µl of corn oil) and or corn oil as a control injection. Twenty four hours later mice were ip injected with LPS or saline as control injection. Numbers in parenthesis indicate sample size. All injections were made separately. Data in FIG. 4 are plotted against changes of $T_b$ during two control days of the mice before injections. The black horizontal bar indicates the dark period in the 12/12 h light/dark cycle. Ambient temperature was 30° C. (thermoneutral for mice). Again, values are means of hourly averages ±SE.

FIG. 5A illustrates the effect of clofibrate, a cytochrome P-450 inducer, on turpentine (100 µl)-induced changes of $T_b$ in mice recorded over 48 hours. At 0900 h (arrowhead) mice were anesthetized (halothane) and sc injected with clofibrate (10 µl in 100 µl of corn oil), and or corn oil as a control injection, and then were sc injected with turpentine. Numbers in parenthesis indicate sample size. All injections were made separately. Data are plotted against changes of $T_b$ during two control days of the mice before injections. The black horizontal bar indicates the dark period on the 12/12 h light/dark cycle. Ambient temperature was 30° C. (thermoneutral for mice). Again, values are means of hourly averages ±SE.

Figure 5B:
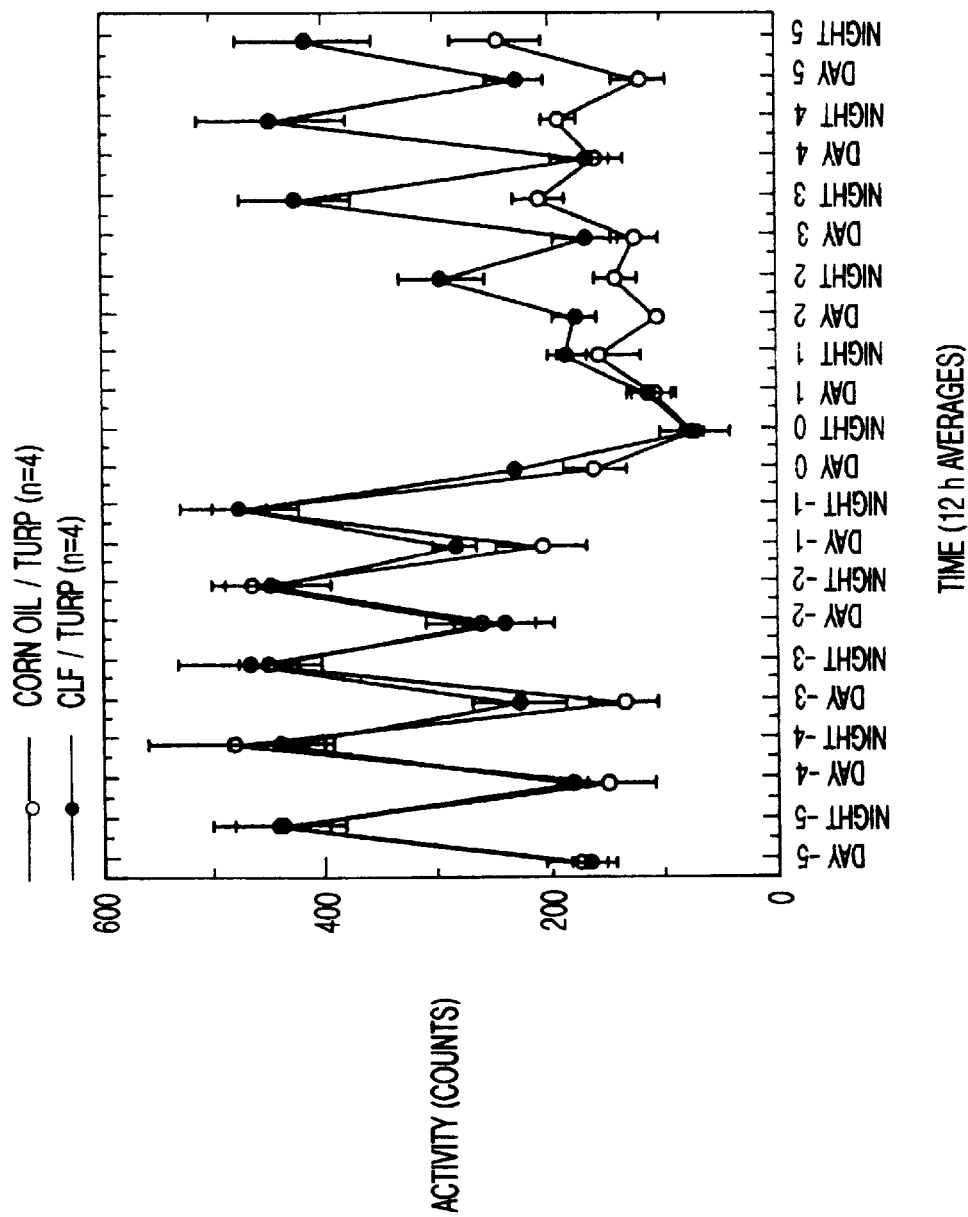
FIG. 5B is a graph showing plots level of physical activity versus time in mice, also illustrating the effects of clofibrate.
Figure 6:
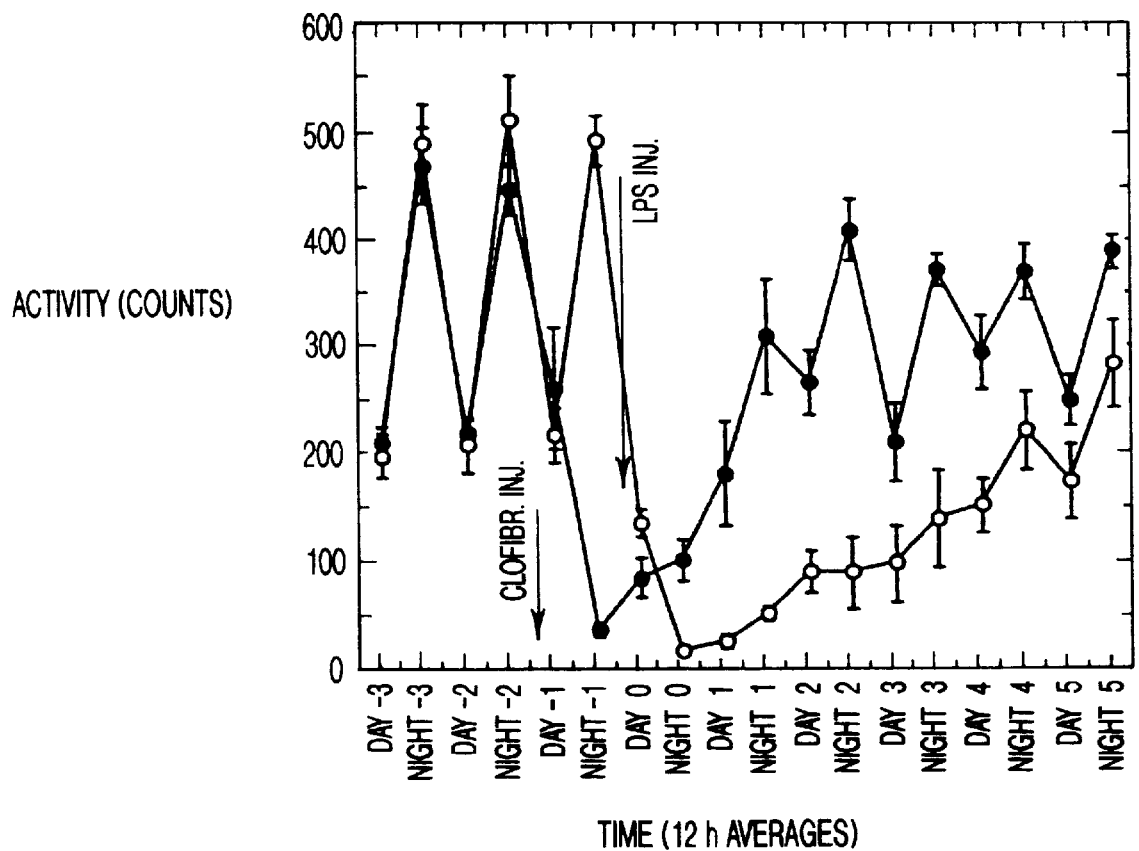
FIG. 6 is another graph showing plots level of physical activity versus time in mice, also illustrating the effects of clofibrate.

Locomotor activity returned towards normal sooner in mice injected with clofibrate. FIG. 5B shows the comparatively rapid rise toward normal activity of the clofibrate-treated animals (closed plotted points). FIG. 6 perhaps is even more illustrative, showing the twelve-hour averages (day and night) of motor activity of mice pre-treated with clofibrate (100 µg/mouse) (closed plotted points) or corn oil as control (open plotted points) ip injection on Day-1. The animals were then ip injected with LPS at a dose of 10 mg/kg on Day 0, twenty-four hours post-clofibrate. The comparatively rapid rise to normal activity levels in the clofibrate-treated animals is apparent.

Figure 7:
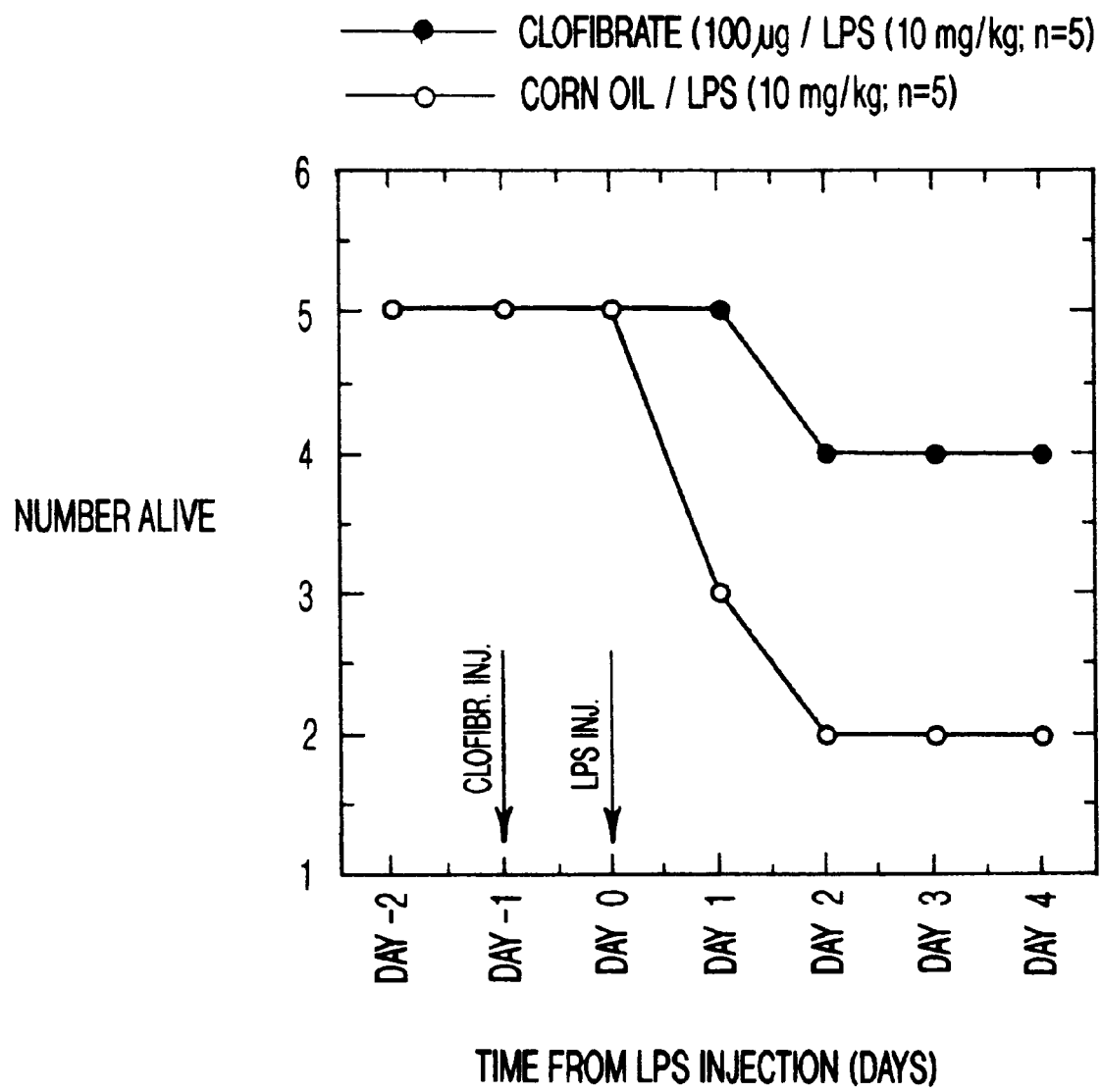
FIG. 7 is a graph plotting mortality versus time from lipopolysaccharide injection in the mice of FIG. 6.

FIG. 7 compares the survival rates, over four days, of treated and control animals from which the data in FIG. 6 was compiled. Mortality in the control animals was markedly elevated, indicating that the toxic effect of LPS was reduced in those mice injected with clofibrate.

Figure 8:
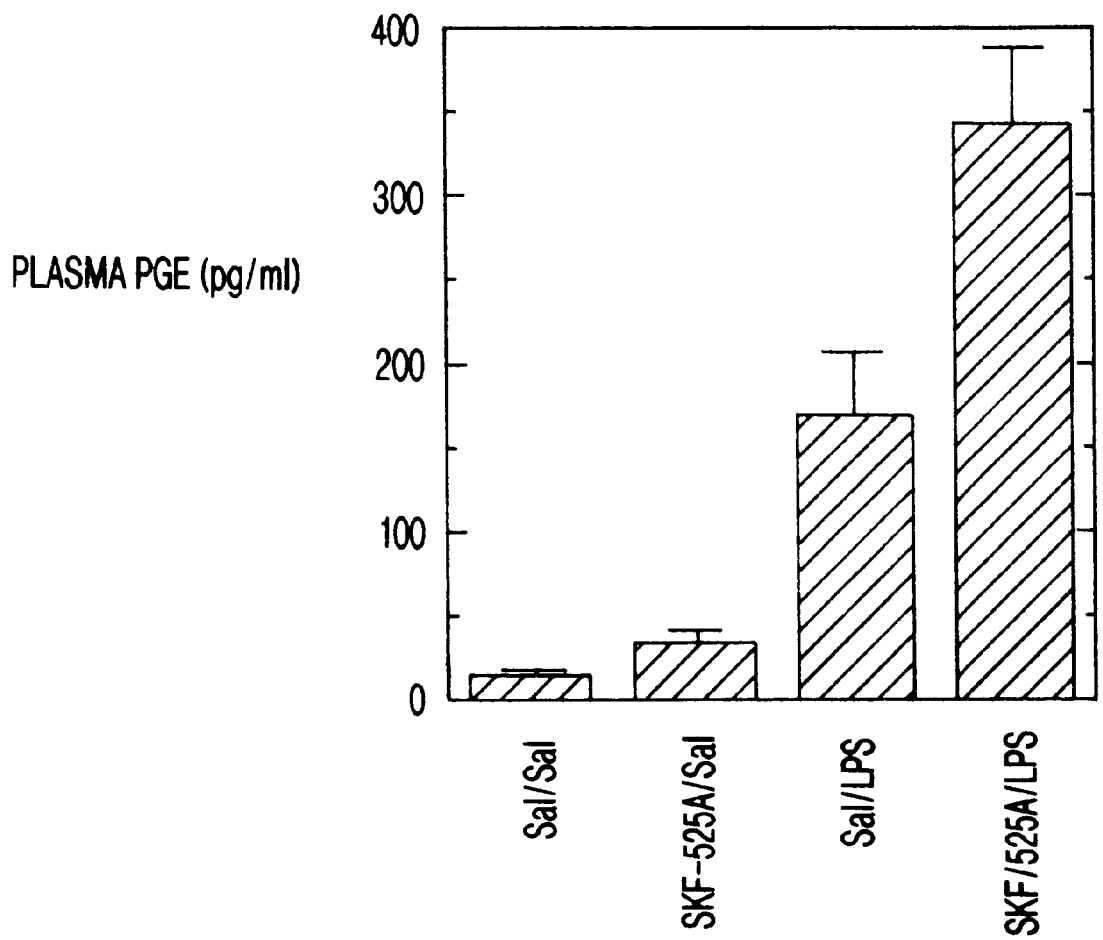
FIG. 8 is a bar graph showing the effect of proadifen on lipopolysaccharide-induced changes in prostaglandin $E_2$ levels in rat plasma.

Injection of an inhibitor of cytochrome P-450 (proadifen, SKF 525-A) ip into rats not only caused larger fevers (as one marker of increased inflammation), but also led to marked increases in circulating concentrations of prostaglandin $E_2$, a major inflammatory mediator. FIG. 8 shows the effect of proadifen on LPS (50 µg/kg; ip injection)-induced changes in prostaglandin $E_2$ in the rat plasma. The inhibition of the cytochrome P-450 pathway accordingly is a method for promoting inflammation.

Also, bezafibrate (4-chlorobenzamidoethyl-phenoxy-2-methylpropanoic acid), an inducer of cytochrome P-450 in the rat, (Boiteux-Antoine A. F., et al., "Comparative induction of drug-metabolizing enzymes by hypolipidaemic compounds", Gen. Pharmacol. 20:407–412 (1989)) was used to ascertain that induction of the enzyme(s) would diminish the symptoms of endotoxin-induced inflammation in the lung. Animals (12-wk old male Brown Norway rats) were treated with bezafibrate (dissolved in sterile corn oil) for two days (intraperitoneal; 1 injection per day; 100 mg/kg/injection) prior to intratracheal instillation of lipopolysaccharide (LPS; 1 mg/rat), then again injected with bezafibrate (100 mg/kg) 24 h and 48 h post-LPS treatment. Body temperature ($T_b$; measured by biotelemetry), lung mucous cell metaplasia, and influx of the inflammatory cells into the lung were evaluated. This course of procedure was used to generate the findings illustrated by FIGS. 9–12.

Figure 9:
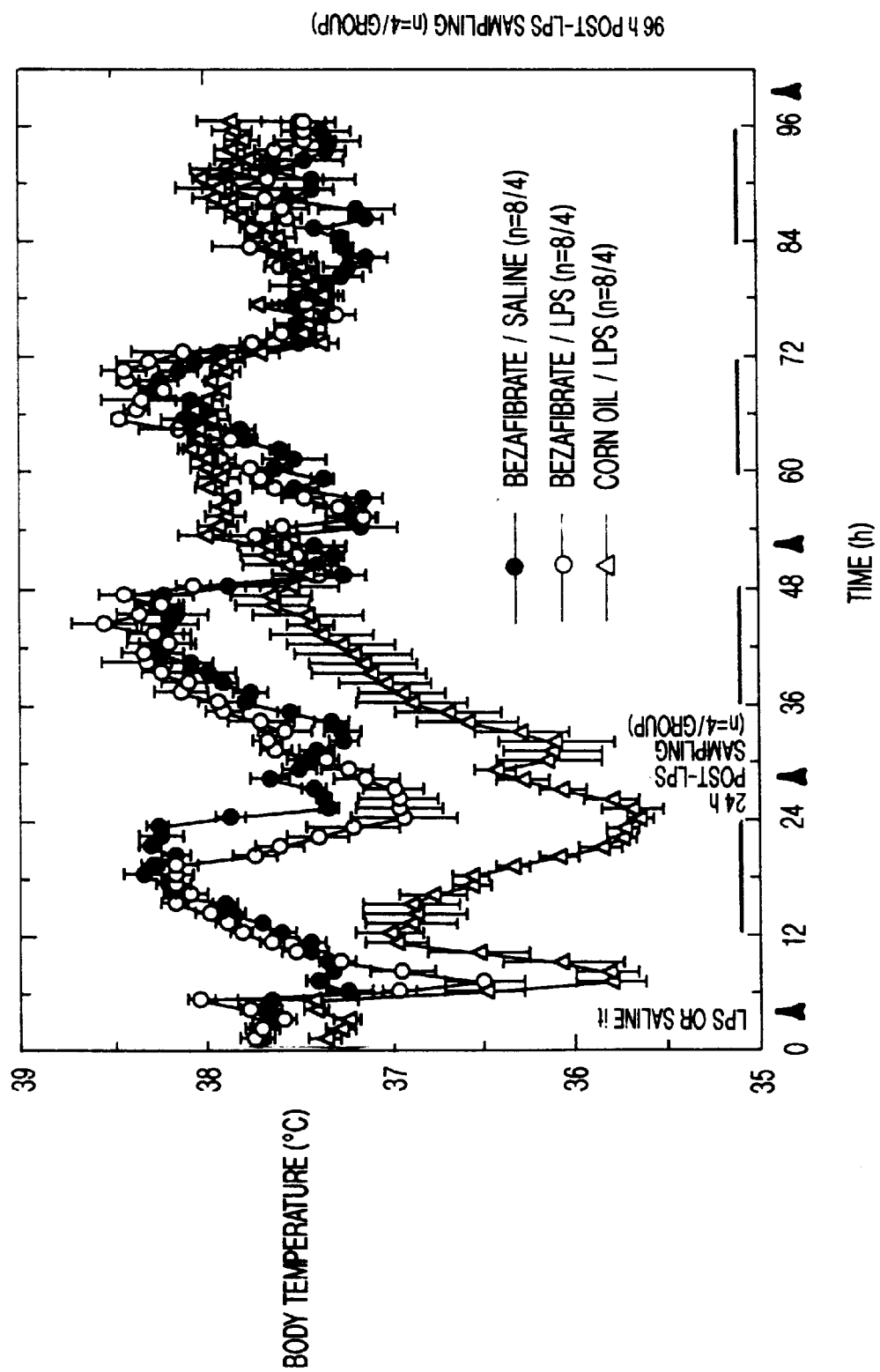
FIG. 9 is a graph showing plots of body temperature versus time in rats, illustrating the effects of bezafibrate, a cytochrome P-450 inducer.

FIG. 9 shows the time-course of $T_b$ (monitored over 4 days; black horizontal bars indicate nighttime in 12/12 h light/dark cycle) of the rats treated intratracheally (it) with LPS (open symbols) and/or saline as a control (closed symbols), and injected with bezafibrate (circles) and/or with corn oil as a control (triangles) as described. As can be seen from FIG. 9, instillation of LPS induced dramatic decrease of $T_b$ in control rats injected with corn oil. Such a drop of $T_b$ in rats can be induced by hypoxia. Therefore, we assumed in this procedure that the LPS-induced decrease of $T_b$ was due to hypoxia produced by inflammation in the lung. Bezafibrate-treated rats, following a brief hypothermic response shortly after the LPS instillation, returned to normal circadian rhythm of $T_b$ indicating a less pronounced and/or better physiologically controlled inflammatory process in those rats. In this procedure, the initial sample size was 8 animals/group. For the evaluation of lung inflammation indices, 4 rats per group were sacrificed 24 h post-LPS, and the other 4/group were sacrificed 95 h post-LPS.

Figure 10:
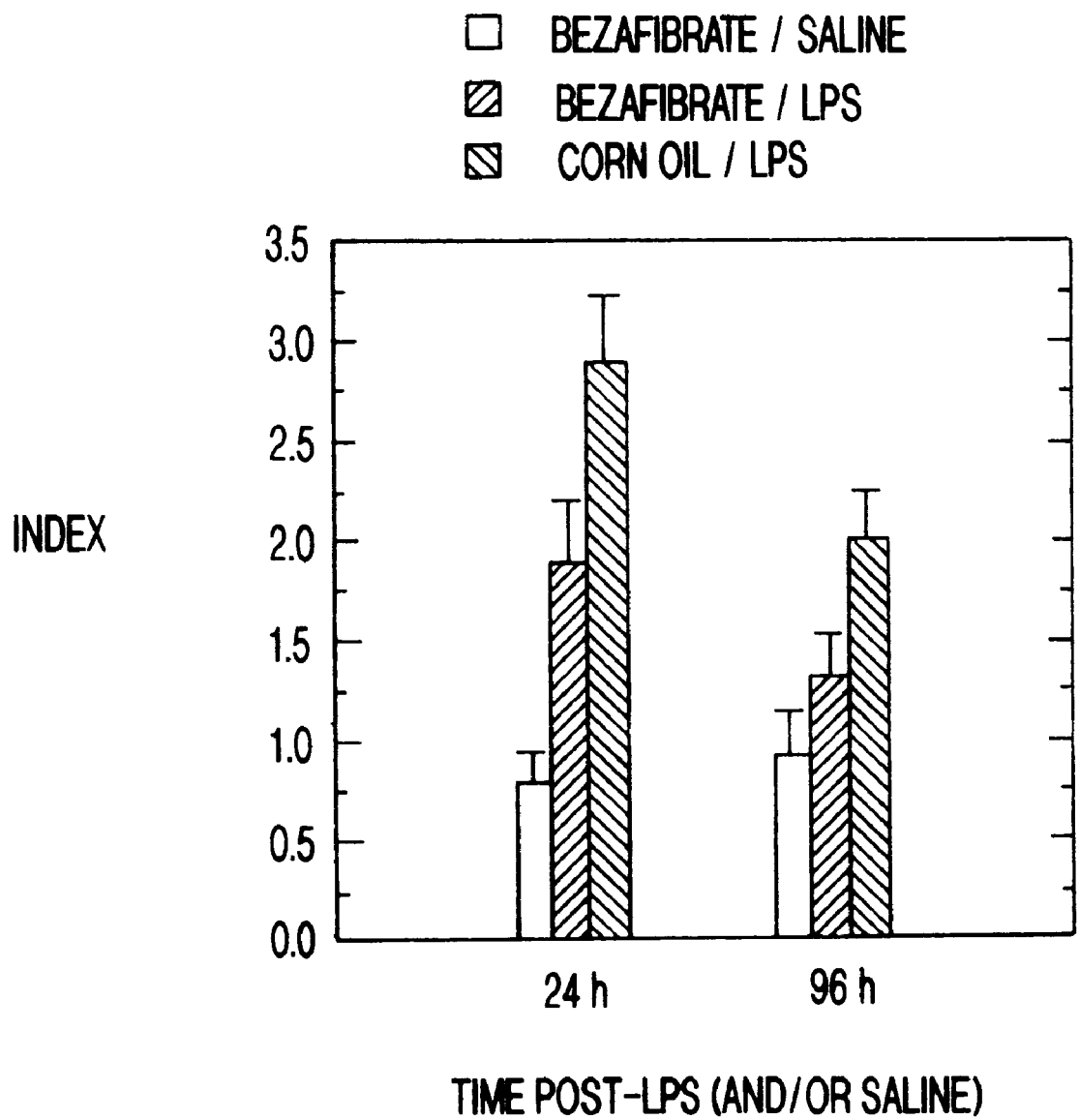
FIG. 10 is a bar graph illustrating the influx of inflammatory cells into the lung tissue of rats on an index-versus-time basis, for rats treated with bezafibrate (lipopolysaccharide induced inflammation) compared to rats treated with corn oil (with lipopolysaccharide induced inflammation)

Reference is made to FIG. 10. The figure presents significant inhibition of the influx of inflammatory cells into the lung tissue of rats treated with bezafibrate/LPS compared to those treated with Corn Oil/LPS (these are the same animals as shown in FIG. 9). Index of the cell influx was estimated 24 h and 96 h after the LPS instillation (n=4/group/time point).

Similarly, FIG. 11 demonstrates index of the inflammation-associated proliferation of mucous cells in the lungs 24 h and 96 h post-LPS of rats treated with bezafibrate and/or corn oil as a control (n=4/group/time point). Bezafibrate inhibited mucous cell metaplasia (growth of new mucous cells) both in large (axial) and small airways.

FIG. 12 illustrates the effect of bezafibrate treatment on the expression of Bcl-2 in LPS-induced metaplastic mucous cells of axial airways of the rat. Lungs for the assay were harvested 96 h post-LPS. Bcl-2 inhibits apoptosis, and presumably allows the metaplastic mucous cells to escape programmed cell death. The percentage of mucous cells expressing Bcl-2 was visibly reduced from 20% in corn oil-treated control rats; (Bcl-2 is exposed as a dark staining on the harvested tissue sections) to less than 3% due to treatment with bezafibrate (percentage of Bcl-2 positive mucous cells, shown as bars ±SD, was calculated from n=5 rats/group).

Because other data have shown that Bcl-2 expression in airway mucous cells is caused by inflammatory factors in the airways (e.g., cytokines and eicosanoids), the foregoing data indicate that injection with bezafibrate altered the type of endotoxin-induced inflammation in the lung; it thus is concluded that cytochrome P-450 pathway participates in inflammation, and that that pharmacological induction of cytochrome P-450 during inflammation has protective effect on severity of the disorder. Inhibition of the pathway facilitates inflammation; induction of the pathway inhibits inflammation.

Thus, the present invention exploits the link determined to exist between expression of cytochrome P-450 and the modulation of inflammation. Cytochromes P-450 are the products of a gene superfamily, in which there are at least 14 mammalian families and 26 subfamilies. These genes are highly inducible (e.g., in the liver) and each P-450 gene produces a single protein. The invention includes, therefore the modulation of inflammation by treating mammals with inhibitors and/or inducers of cytochrome P-450. Furthermore, a systemic treatment of the rat with known pharmacological inducers of P-450 reduces some indices of lung inflammation following intratracheal instillation of LPS.

Specifically, with respect to lung inflammation, the inventive treatment reduces (i) infiltration of the lungs by inflammatory neutrophils and (ii) mucous cell metaplasia, which is accompanied by decreased Bcl-2 expression (a gene that inhibits apoptosis) in the mucous cells. It is uncertain which tissues and cells are affected in the generation of these anti-inflammatory effects in the lung due to systemic administration of P-450 inducers. Increased expression of the particular P-450 isoform(s) due to administration of the P-450 inducer likely affects either the production of chemotaxic pro-inflammatory/pro-febrile mediators in the lung (e.g., interleukin-8), or influences the sensitivity of peripheral inflammatory cells (e.g., neutrophils) to chemotaxic factors generated by lung cells exposed to inflammatory agents. Rat P-450 isoforms known to catalyze the epoxidation of arachidonic acid are CYP1A1, CYP1A2, CYP2B1, CYP2B2, and CYP2C11.

There are many potential pathways by which induction of P-450 reduces inflammation. One mechanism likely involves cyclooxygenase-2 (COX-2). Data that suggest a link between P-450 and COX-2 are, among others: (1) mucous cell proliferation results from the suppression of apoptosis: overexpression of COX-2 inhibits apoptosis, while inducers of P-450 prevent proliferation; (2) mucous production is dependent on prostaglandin generation, and an inhibitor of P-450, proadifen, enhanced the LPS-induced $PGE_2$ synthesis (apparent link between P-450 and cyclooxygenases); (3) COX-2 is inducible by inflammatory stimuli: overexpression of the enzyme is associated with synthesis of IL-8 among other cytokines, and with extravasation of the inflammatory cells.

The utility of the invention is established in part upon a rat model of the lung inflammation induced by lipopolysaccharide. Constituents of endotoxin of the cell walls of gram-negative bacteria, LPSs are potent environmental agents that have pro-inflammatory properties and therefore can obstruct and inflame airways. LPS has a broad range of actions, including the activation of endothelial and epithelial cells, neutrophils, and alveolar macrophages, and the induction of cytokines, prostaglandins, leukotrienes and other inflammatory mediators. Airway infections induced by endotoxin-laden bacteria in hospitalized patients are associated with fever, influx of inflammatory cells (particularly neutrophils), and increased production of respiratory mucus. The invention stems in part from a determination that intra-airway exposure to LPS induces inflammatory changes in the rat and mouse, similar to changes in patients with chronic bronchitis, bronchopneumonia, and cystic fibrosis, supporting a conclusion that the present invention is useful in the treatment of the foregoing diseases.

The invention also is based in part upon a finding that the involvement of P-450 in thermoregulatory responses during inflammation indicates that treatment with inducers of P-450 is accompanied by prevention of anapyrexia and fever, while inhibitors of P-450 augment febrile and anapyrexic responses. Inhibitors and inducers of P-450 affect the measured inflammatory features in mice and rats in the manner that substantiates the determination that inducers of P-450 diminish, while inhibitors exacerbate, inflammation.

Because the LPS-induced lung inflammation of Brown Norway rats (it-instillation of saline solution of LPS) is correlated with the rapid influx of inflammatory cells into the lungs, this animal model is used to demonstrate the utility of the invention.

INDUSTRIAL APPLICABILITY

The invention is further illustrated by the following non-limiting examples.

Example 1

It instillation of endotoxin induces a drop in body temperature (anapyrexia) followed by fever in rats: both responses are prevented by bezafibrate, and enhanced by 1-aminobenzitriazole, an inducer and inhibitor of P-450, respectively.

FIG. 9 depicts changes in body temperature over time (4 days) of Brown Norway rats instilled intratracheally with LPS (or saline as a control) at a dose of 1 mg/rat, and injected with bezafibrate (100 mg/rat/injection) 24 h prior to LPS, then post-LPS as shown by the arrows. LPS (1 mg/rat) was instilled 3–4 h after time 0 (between 9:00 and 10:00 am). Body temperatures of rats were recorded for several days before and after the LPS instillation at 5 minute intervals using a biotelemetry system. Treatment with bezafibrate (Sigma), a P-450 inducer, blocked the post-LPS drop of body temperature in rats (lasting up to 48 h post-LPS in control rats), and prevented fever seen between 48 and 60 h post-LPS in the control animals. In this particular example, bezafibrate was dissolved in a sterile corn oil (Sigma) and injected intraperitoneally. Bezafibrate dissolved in an aqueous solution of 0.01 M anhydrous sodium carbonate (pH ~8) and injected im, also prevents fever in rats (data not shown). Horizontal bars indicate the dark period in 12/12 h light/dark cycle. Values are means of hourly averages ±SE. Numbers in parentheses indicate sample size.

Example 2

Figure 13:
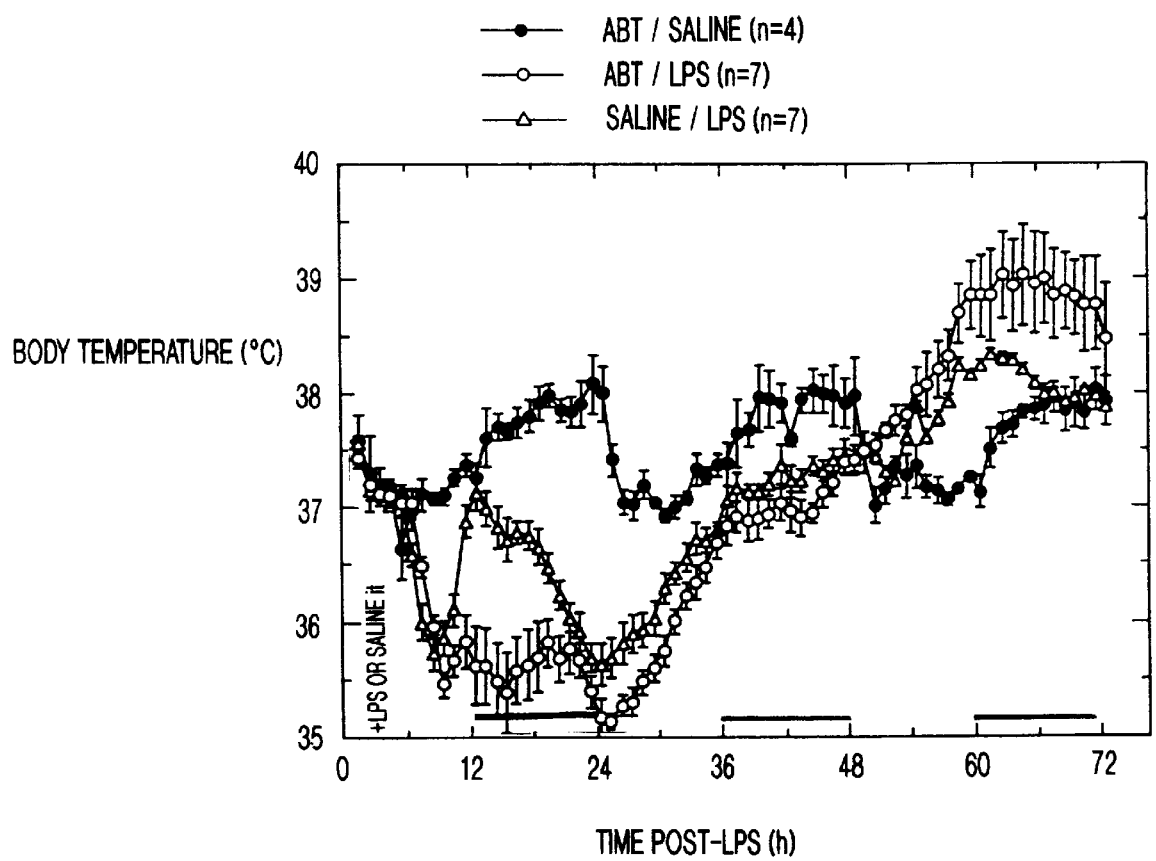
FIG. 13 is a graph showing plots of body temperature versus time in rats, illustrating the effects of 1-aminobenzotriazole.

A similar procedure was followed to show the effect of the inhibitor of cytochrome P-450 on changes of body temperature of rats instilled it with LPS. 1-Aminobenzotriazole (ABT; Sigma) was selected because it inhibits P-450 protein in pulmonary microsomes. Furthermore, the agent is water soluble and relatively nontoxic on chronic administration. FIG. 13 demonstrates the findings of this example. ABT was injected im 24 prior to LPS, and as shown in figure (each injection 100 mg/kg). As in the experiment shown in FIG. 9, LPS (1 mg/rat) was instilled 3–4 h after time 0 (between 9:00 and 10:00 am). ABT (100 mg/kg) was injected 24 h prior to LPS, and as indicated (arrowheads). Horizontal bars indicate the dark period in 12/12 h the light/dark cycle. Values are means of hourly averages ±SE. Numbers in parentheses indicate sample size. It is noted that ABT potentiated the initial drop of body temperature in LPS-exposed rats, and also enhanced a subsequent fever. Three out of seven animals treated with LPS and ABT unexpectedly died during extremely high fevers. That ABT exacerbates fever in rats instilled it with LPS suggests that cytochrome P-450s (presumably epoxygenases) contribute to controlling the height of fever during inflammation. It therefore is postulated that during lung inflammation the use of drugs that inhibit epoxygenase as a side effect, may have deleterious influence on the recovery and well-being of patients.

Example 3

Figures 11A, 11B:
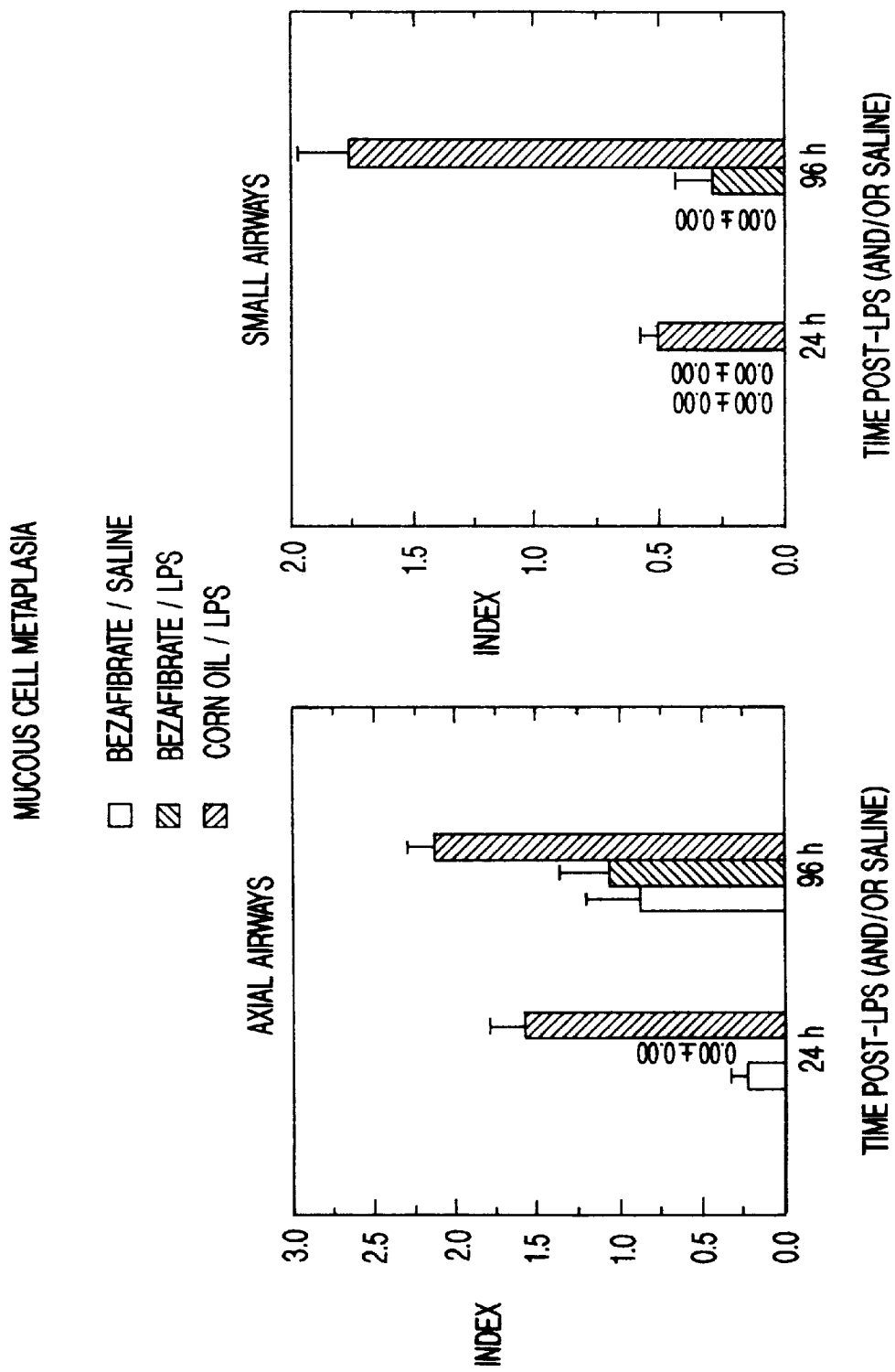
FIGS. 11A and 11B are bar graphs demonstrating the index of the inflammation-associated proliferation of mucous cells in the large (axial) and small airways, respectively, in lungs of rats treated with bezafibrate and/or corn oil.

Treatment with bezafibrate, an inducer of P-450, results in reduction of LPS-induced influx of inflammatory cells, mucous cell metaplasia, and Bcl-2 expression. It was determined that instillation of endotoxin induces an increase in neutrophils into the lung of rats, and that the Bcl-2 gene is expressed in LPS-induced metaplastic mucous cells in the lungs of rats. Brown Norway rats were treated with bezafibrate and it exposed to LPS according to the procedure of Example 1. Lung samples were collected 24 h and 96 h post-LPS. Necropsy, tissue preparation for histopathology, and immunohistochemistry were performed, including treatment of lung epithelium with alcian blue. FIGS. 10, 11, and 12 demonstrate findings of this example. FIG. 10 illustrates the significant inhibition of the influx of neutrophils into the lung tissue of rats treated with bezafibrate/LPS compared to those treated with corn oil/LPS. FIGS. 11A and 11B show the changes of the observed alcian blue-positive (mucus-producing) cells in the lung epithelium of rats exposed it to LPS and treated with bezafibrate (100 mg/kg) compared to those treated with corn oil/LPS as a control. Tissue sections were used from four rats, sacrificed 24 and 96 h after the LPS instillation.

FIG. 12 illustrates the effect of bezafibrate treatment (100 mg/kg, as in Example 1) on the expression of Bcl-2 in LPS-induced metaplastic mucous cells of axial airways of the rat. Lungs for the assay were harvested 96 h post-LPS. The percentage of mucous cells expressing Bcl-2 was reduced from 20% (in LPS-corn oil-treated rats) to less than 3% due to treatment with bezafibrate. The percentage of Bcl-2 positive mucous cells, shown as bars ±SD, was calculated from n=5 rats/group.

These data indicate that treatment with a P-450 inducer: 1) diminished the LPS provoked influx of inflammatory cells into the lungs (FIG. 10); 2) reduced the LPS-induced mucous cell metaplasia in the axial and small airways (FIGS. 11A and 11B); and 3) suppressed the LPS-induced expression of a Bcl-2 protein in the mucous cells (FIG. 12).

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of modulating inflammation in a mammal, comprising the step of regulating the mammal's cytochrome P-450 pathway.

2. A method according to claim 1 wherein regulating the mammal's cytochrome P-450 pathway comprises reducing inflammation by inducing the cytochrome P-450 pathway.

3. A method according to claim 2 wherein the step of inducing the cytochrome P-450 pathway comprises treating the mammal with a substance selected from the group consisting of bezafibrate and clofibrate.

4. A method according to claim 3 wherein the step of reducing inflammation comprises the step of injecting the substance to reduce inflammation in the mammal's lungs.

5. A method according to claim 1 wherein regulating the mammal's cytochrome P-450 pathway comprises increasing inflammation by inhibiting the cytochrome P-450 pathway.

6. A method according to claim 5 wherein the step of inhibiting the cytochrome P-450 pathway comprises treating the mammal with a substance selected from the group consisting of proadifen, econazole, clotrimazole, and 1-aminobenzotriazole.

7. A method of modulating inflammation in a mammal, comprising the steps of:

selecting a substance from the group of substances which regulate the cytochrome P-450 pathway; and injecting the mammal with the selected substance.

8. A method according to claim 7 wherein the step of selecting a substance comprises selecting a substance from the group consisting of bezafibrate and clofibrate.

9. A method according to claim 7 wherein the step of selecting a substance comprises selecting a substance from the group consisting of proadifen, econazole, clotrimazole, and 1-aminobenzotriazole.

10. A method of preventing or reducing pulmonary inflammation in a mammal, comprising the step of deliberately inducing the mammal's cytochrome P-450 pathway.

11. A method according to claim 10 wherein the step of deliberately inducing the mammal's cytochrome P-450 pathway comprises the steps of:

selecting a substance from the group consisting of bezafibrate and clofibrate; and injecting the substance.

* * * * *